United States Patent
Huby et al.

(10) Patent No.: US 10,799,657 B2
(45) Date of Patent: Oct. 13, 2020

(54) POWER MANAGEMENT IN RESPIRATORY TREATMENT APPARATUS

(71) Applicant: ResMed Pty Ltd, Bella Vista (AU)

(72) Inventors: Ronald James Huby, North Epping (AU); Andrew Roderick Bath, Quakers Hill (AU); John David Oates, Castle Hill (AU)

(73) Assignee: ResMed Pty Ltd (AU)

( * ) Notice: Subject to any disclaimer, the term of this patent is extended or adjusted under 35 U.S.C. 154(b) by 1126 days.

(21) Appl. No.: 14/472,651

(22) Filed: Aug. 29, 2014

(65) Prior Publication Data

US 2014/0366876 A1   Dec. 18, 2014

Related U.S. Application Data

(63) Continuation of application No. 13/060,566, filed as application No. PCT/AU2009/001168 on Sep. 7, 2009, now Pat. No. 8,844,522.

(Continued)

(51) Int. Cl.
  *A61M 16/00*   (2006.01)
  *A61M 16/16*   (2006.01)
  (Continued)

(52) U.S. Cl.
  CPC .... *A61M 16/0003* (2014.02); *A61M 16/0069* (2014.02); *A61M 16/024* (2017.08);
  (Continued)

(58) Field of Classification Search
  CPC .......... A61M 16/0069; A61M 16/1075; A61M 16/1085; A61M 16/109; A61M 16/16;
  (Continued)

(56) References Cited

U.S. PATENT DOCUMENTS

| 4,218,644 A | 8/1980 | Bourke et al. |
| 4,639,609 A | 1/1987 | Floyd et al. |

(Continued)

FOREIGN PATENT DOCUMENTS

| DE | 10017193 A1 | 11/2001 |
| EP | 2055336 A1 | 5/2009 |

(Continued)

OTHER PUBLICATIONS

"Look-up Table Model" and "Current", Comprehensive Dictionary of Electrical Engineering (2nd ed. 2005). http://s1.nonlinear.ir/epublish/book/Comprehensive_Dictionary_of_Electrical_Engineering_0849330866.pdf (Accessed Dec. 18, 2019). (Year: 2005).*

(Continued)

*Primary Examiner* — Peter S Vasat
(74) *Attorney, Agent, or Firm* — Botos Churchill IP Law LLP

(57) ABSTRACT

A respiratory treatment apparatus provides respiratory treatment with improved power management control to permit more efficient power consumption and power supply units, such as battery powered operation. In one embodiment, power management prioritizes the flow generator (104) over other accessories such as the heating elements (111, 135) of a humidifier (112) and/or a delivery tube. The flow generator may control operations of the heating elements as a function of a detected respiratory cycle. For example, the timing of operation of the heating elements may be interleaved with the portion of an inspiratory phase of the respiratory cycle to permit the flow generator to operate during a peak power operation without a power drain or with a lower power drain from these components. Operations of distinct sets of components of the system (e.g., different heating elements) may also be interleaved to prevent simultaneous peak power operations.

17 Claims, 11 Drawing Sheets

Related U.S. Application Data

(60) Provisional application No. 61/095,714, filed on Sep. 10, 2008.

(51) Int. Cl.
*A61M 16/10* (2006.01)
*A61M 16/06* (2006.01)
*A61M 16/12* (2006.01)
*H02J 1/14* (2006.01)

(52) U.S. Cl.
CPC ...... *A61M 16/109* (2014.02); *A61M 16/1085* (2014.02); *A61M 16/1095* (2014.02); *A61M 16/16* (2013.01); A61M 16/0666 (2013.01); A61M 16/107 (2014.02); A61M 16/12 (2013.01); A61M 16/161 (2014.02); A61M 2016/0027 (2013.01); A61M 2016/0039 (2013.01); A61M 2202/0208 (2013.01); A61M 2205/3368 (2013.01); A61M 2205/502 (2013.01); A61M 2205/52 (2013.01); A61M 2205/8212 (2013.01); A61M 2205/8262 (2013.01); *H02J 1/14* (2013.01)

(58) Field of Classification Search
CPC ............ A61M 16/161; A61M 2205/33; A61M 2205/36; A61M 2205/50; A61M 2205/502; A61M 2205/8212; A61M 2205/8262; H02J 1/14
See application file for complete search history.

(56) References Cited

U.S. PATENT DOCUMENTS

| | | | |
|---|---|---|---|
| 4,944,310 A | | 7/1990 | Sullivan |
| 5,583,419 A | | 12/1996 | Haller |
| 5,712,795 A | | 1/1998 | Layman et al. |
| 5,741,307 A | | 4/1998 | Kroll |
| 5,835,366 A | * | 11/1998 | Pleso ............... H02J 7/0065 363/59 |
| 5,902,054 A | | 5/1999 | Coudray |
| 5,929,538 A | | 7/1999 | O'Sullivan et al. |
| 6,635,021 B1 | | 10/2003 | Sullivan et al. |
| 7,073,500 B2 | | 7/2006 | Kates |
| 7,080,645 B2 | | 7/2006 | Genger et al. |
| 7,314,046 B2 | | 1/2008 | Schroeder et al. |
| 8,156,937 B2 | | 4/2012 | DeVries et al. |
| 2003/0154977 A1 | | 8/2003 | White et al. |
| 2003/0181953 A1 | | 9/2003 | Dropps et al. |
| 2006/0033482 A1 | | 2/2006 | Florence et al. |
| 2006/0042638 A1 | | 3/2006 | Niklewski et al. |
| 2007/0050898 A1 | * | 3/2007 | Larson ............... A41D 13/1209 2/456 |
| 2007/0125376 A1 | | 6/2007 | Reinstadtler |
| 2007/0150019 A1 | | 6/2007 | Youker et al. |
| 2007/0277825 A1 | | 12/2007 | Bordewick et al. |
| 2008/0099017 A1 | | 5/2008 | Bordewick et al. |
| 2008/0149101 A1 | | 6/2008 | Becker et al. |
| 2008/0238205 A1 | * | 10/2008 | Lee .................. H02J 9/061 307/66 |
| 2010/0065054 A1 | * | 3/2010 | Bowman ............ A61M 16/00 128/204.21 |
| 2010/0132707 A1 | | 6/2010 | Muller |

FOREIGN PATENT DOCUMENTS

| | | |
|---|---|---|
| JP | 9065579 A | 3/1997 |
| JP | 2005270680 A | 10/2005 |
| JP | 2006254317 A | 9/2006 |
| WO | 2000069012 A1 | 11/2000 |
| WO | 0113981 A1 | 3/2001 |
| WO | 2001078449 A1 | 10/2001 |
| WO | 2006050384 A2 | 5/2006 |
| WO | 2007019628 A1 | 2/2007 |
| WO | 2007045017 A2 | 4/2007 |
| WO | 2007121736 A2 | 11/2007 |
| WO | 2010003064 A1 | 1/2010 |

OTHER PUBLICATIONS

Chinese Search Report for Application CN201510222649.2 dated Jun. 13, 2017.
Yonghong, W. et al., STM32 Series ARM Cortex-M3 Microcontroller Principle and Practice, Jul. 2008, p. 20, Section 1.4.6, Beijing: Beihang University Press.
Extended European Search Report for Application No. EP09812520 dated Oct. 28, 2015.
International Search Report, PCT/AU2009/001168, dated Jan. 28, 2010.

* cited by examiner

POWER MANAGEMENT IN RESPIRATORY TREATMENT APPARATUS

CROSS-REFERENCE TO RELATED APPLICATIONS

The present application is a continuation of U.S. patent application Ser. No. 13/060,566, filed on Feb. 24, 2011, which application is a national phase entry under 35 U.S.C. § 371 of International Application No. PCT/AU2009/001168, filed Sep. 7, 2009, which claims priority from U.S. Provisional Patent Application No. 61/095,714, filed Sep. 10, 2008, the disclosure of which is hereby incorporated herein by reference.

FIELD OF THE TECHNOLOGY

The present technology relates to apparatus for treatment of respiratory conditions such as the conditions related to obstructive sleep apnea (OSA), sleep disordered breathing (SDB), allergy induced upper airway obstruction or early viral infection of the upper airway. More particularly, the technology involves improved power management in such respiratory treatment apparatus.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with OSA are also likely to disturb their partner's sleep. The best form of treatment for patients with OSA is continuous positive airway pressure (CPAP) applied by a flow generator such as a blower (compressor) via a connecting delivery hose with a patient interface. The positive pressure can prevent a collapse of the patient's airway during inspiration, thus preventing events such as snoring, apnoeas or hypopnoeas and their sequelae.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A pressure setting during expiration lower than inspiration may generally be referred to as expiratory pressure relief. As described by Sullivan in U.S. Pat. No. 4,944,310, positive airway pressure treatments typically provide gas under pressures to the patient in the range of 4 to 15 cmH$_2$O from the device and may involve flow rates of at about 120 liters/minute. Some of the air will escape via an end restriction and not be delivered to the patient. These pressure settings may also be adjusted based on the detection of conditions of the patient's airway. For example, treatment pressure may be increased in the detection of partial obstruction, apnea or snoring.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

Respiratory treatment apparatus are sometimes provided with accessory components for comfort conditioning of the flow or pressurized air supplied by the flow generator. For example, the supplied air may be applied to a humidifier to humidify and warm the treatment gas prior to its delivery to a patient. Similarly, various heating elements can be connected with a delivery conduit to help in maintaining a particular temperature of the supplied gas as it is conducted to the patient from a supply unit or humidifier.

These elements can place a significant demand for power during operations of the device. It may be desirable to develop these devices for treating upper respiratory conditions with improved design efficiencies.

SUMMARY OF THE TECHNOLOGY

In an aspect of the present technology, apparatus and methods provide respiratory treatment for a patient.

In another aspect of the present technology, a respiratory treatment apparatus provides a flow or pressurized gas that may be heated and/or humidified for patient comfort.

In another aspect of the technology, a respiratory treatment apparatus includes power management technology.

In one embodiment, a respiratory treatment apparatus includes a flow generator, an accessory device, a power supply unit and a controller. The controller may be coupled with the flow generator, the accessory apparatus, and the power supply unit. The controller is configured to control offsetting of peak power operations of the flow generator and the accessory apparatus as a function of a respiratory cycle of the respiratory treatment device. The accessory apparatus may be for example, a heating element, humidifier or delivery tube heater. In a further embodiment, the controller controls the offsetting of peak power operations of the flow generator and the accessory apparatus during an inspiratory rise time of an inspiratory phase. The controller may optionally control permitting concurrent operations of the accessory apparatus and the flow generator during a remaining inspiratory time of the inspiratory phase. With this type of power management, the controller may substantially avoid simultaneous peak power operations of the flow generator and the accessory apparatus. In such an embodiment, the controller may include a power prioritization algorithm or module that prioritizes operations to classify the flow generator as a greater priority than a priority classification of the accessory apparatus.

In an example embodiment, the flow generator comprises a servo-controlled blower and the accessory apparatus comprises a heater of a humidifier and/or a heater of a delivery tube. Optionally, the controller may synchronize de-powering of the heating element of either or both of a humidifier or delivery tube heater during an increase in a speed of the blower. Moreover, a controller of the device may be configured to set a variable power level of the heater of the humidifier and/or a heater of a delivery tube. Still further, the controller may control interleaving of the operations of the heater of the humidifier and the heater of the delivery tube. This may be accomplished with pulse width modulated signals that are offset in time.

In another embodiment, the respiratory treatment device with a flow generator, a delivery tube heater, a humidifier heater and a power supply unit, has a controller that interleaves the operations of the delivery tube heater and the humidifier heater and thereby substantially avoids simultaneous peak power operations of the delivery tube heater and the humidifier heater.

In another respiratory treatment device embodiment, the device implements a method including (a) controlling a flow generator to provide a flow of breathable gas to a patient, (b) controlling a heater element of a flow path of the flow generator, and (c) controlling the heater element as a function of a respiratory cycle of the respiratory treatment device. The device may further implement the method by controlling offsetting of peak power operations of the flow generator and the heater element as a function of a respiratory cycle of the respiratory treatment device. The method may further include controlling an offset of respective operations of the flow generator and the heater during an inspiratory rise time of an inspiratory phase while permitting concurrent operations of the heater and the flow generator during a remaining inspiratory time of the inspiratory phase.

In a still further embodiment, a method of a respiratory treatment device, includes at least one or more of the steps of (a) controlling a flow generator to provide a flow of breathable gas to a patient, (b) controlling a first heater of a flow path of the flow generator, (c) controlling a second heater of a flow path of the flow generator, and (d) controlling a first offset of respective operations of the first and second heaters. In one embodiment, the first offset comprises interleaving the operations of the heater elements by generating pulse width modulated control signals to the heater elements such that the pulse width modulated control signals of one heater are offset in time from the pulse width modulated control signals of the other heater element. Optionally, the method may further include controlling a second offset of respective operations of the flow generator and the first and second heaters during an inspiratory rise time of an inspiratory phase while permitting concurrent operations of at least one of the first and second heaters and the flow generator during a remaining inspiratory time of the inspiratory phase.

Further embodiments and features of the present technology will be apparent from the following detailed disclosure, abstract, drawings and the claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
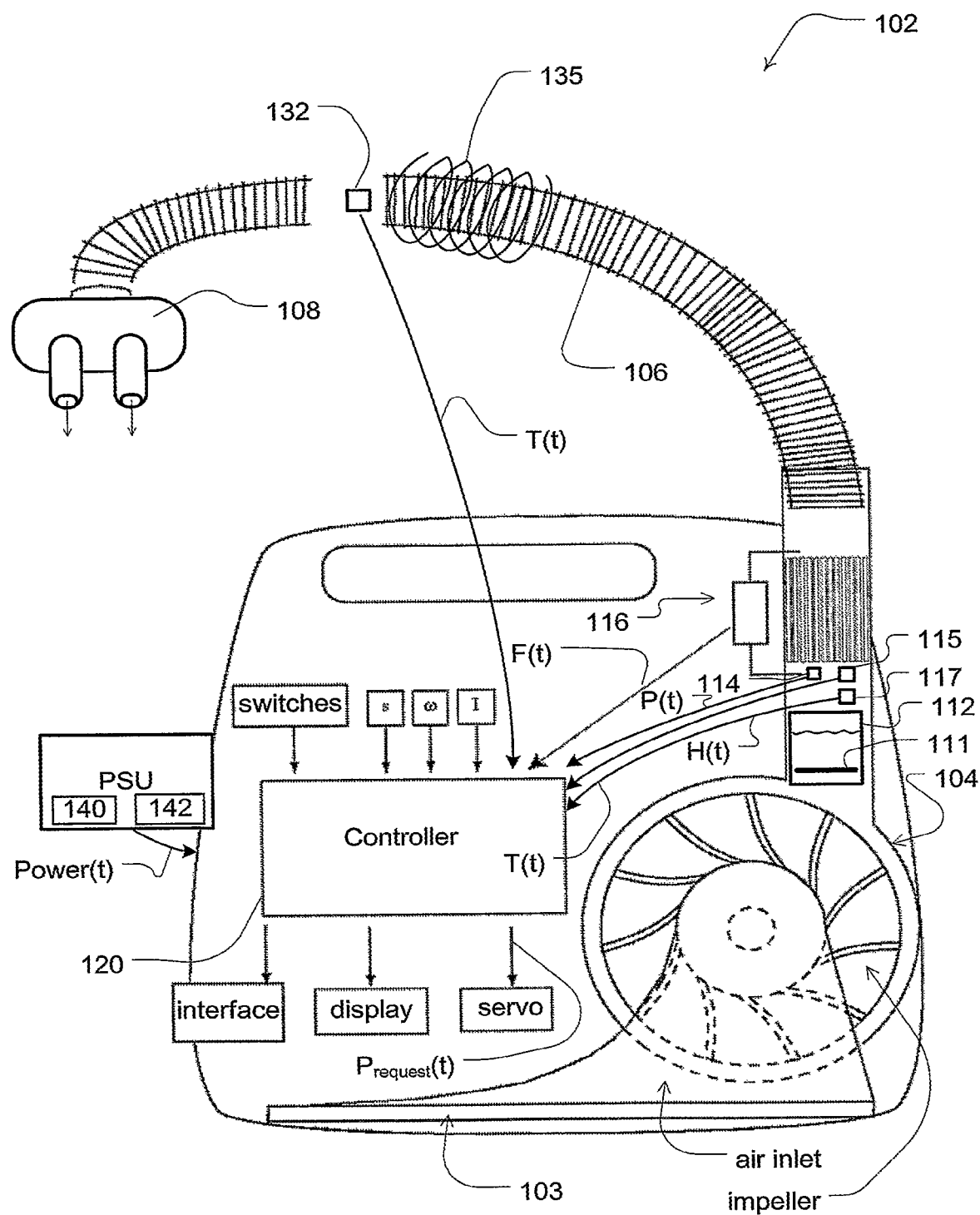
FIG. 1 shows example components of an apparatus for respiratory treatment of the upper airway of a patient.
Figure 2:
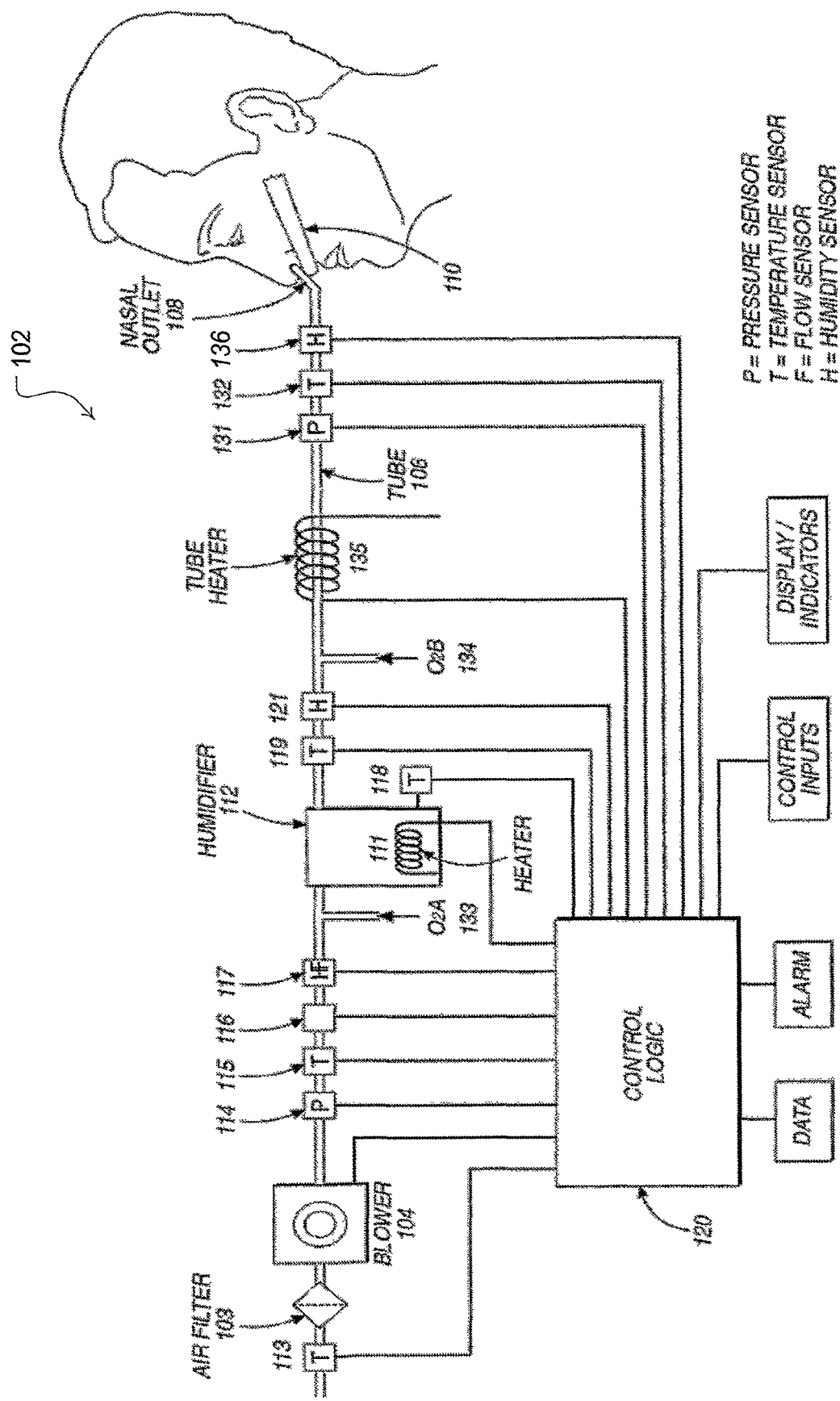
FIG. 2 illustrates an embodiment of a control relationship of components of the apparatus for respiratory treatment of FIG. 1.

The embodiments of the present power management technology may be implemented as a respiratory treatment device 102 that may include some or all of the components illustrated in FIGS. 1 and 2. For example, the respiratory treatment device will typically include a flow generator such as a servo-controlled blower 104. The blower 104 will typically include an air inlet and impeller driven by a motor (not shown). Optionally, the air inlet may be coupled with a gas supply 133, 134, such as for oxygen, to mix with or supplement the breathable gas supplied by the impeller to the airway of a user. Moreover, an air filter 103 may be provided, such as a HEPA filter, to remove dust or other allergens from the air drawn into the air inlet. The blower may optionally be configured for generating varied flows or varied pressures associated with a patient respiratory cycle depending on the type of treatment (e.g., continuous level, bi-level, varying level etc. such as a pressure in an example range of 4 to 15 cmH$_2$O or 4 to 25 cmH$_2$O) and it may further be adjusted based on respiratory conditions (e.g., apnea, hypopnea, obstruction, etc.) detected by the apparatus (e.g., apnea, hypopnea, obstruction, etc.).

The respiratory treatment device 102 will also typically include a patient interface such as a flow delivery conduit 106 and nasal prongs or nasal cannula 108 to carry the flow of air or breathable gas to the upper airway of a user of the device or patient. The blower 104 can be coupled with the air delivery conduit 106 and the nasal cannula 108 so as to provide the breathable gas from the blower 104. Optionally, the patient interface may include a mask (not shown) coupled with the delivery conduit.

The respiratory treatment device may also optionally include one or more pressure sensors 114, 131 such as a pressure transducer. The pressure sensor 114 can be configured to measure the pressure generated by the blower 104 and/or supplied at the nasal cannula or patient airway. In the illustrated embodiment, the pressure sensor 114 is proximate to the blower 104. An additional or alternative pressure sensor 131 may be located downstream of the blower such as in the patient interface. The pressure sensor generates a pressure signal p(t) indicative of the measurements of pressure at its particular location.

In some embodiments, the respiratory treatment delivery device may optionally include one or more flow sensors 116. For example, flow through the nasal cannula 112 may be measured using a pneumotachograph and differential pressure transducer or similar device such as one employing a bundle of tubes or ducts to derive a flow signal F(t).

Although the flow sensor is illustrated in FIG. 1 in a location proximate to the blower, the flow sensor may optionally be located closer to the patient, such as in the patient interface or nasal cannula 108.

Optionally, the patient interface and/or blower may also include accessory devices for patient comfort such as a humidifier 112 and humidifier heater 111. The humidifier device may be configured or controlled to heat and/or humidify the breathable gas to a desired temperature and/or humidity. For example, the device may include a reservoir or fluid circuit for passing the breathable gas through or proximate with a fluid or vapor of the reservoir or fluid circuit. The heater 111 may include one or more heating elements and/or heating plates to heat the fluid to create the vapor. In one embodiment, the heater may be based on a film laminate heater that may be fitted by adhesive to the base of a heater plate. The heater element may include a temperature sensor on the heater film. As a further option, while the heater 111 is in contact with the liquid of the reservoir of the humidifier, an additional heater that is not in contact with the liquid of the reservoir may also heat the breathable gas from the flow generator that passes through the humidifier.

Additional accessory devices may also be implemented with the respiratory treatment device. For example, a heater or heating element(s) such as a delivery tube heater 135 may optionally be provided in or on the delivery tube of the patient interface to assist in maintaining the temperature of the breathable gas after it passes from the humidifier or flow generator. By keeping the delivery conduit warm, condensation in the delivery tube may be reduced or avoided as the breathable gas traverses the delivery tube toward the patient. Optionally, the heating devices may further include a pump for circulating warmed fluid within the reservoir or within a fluid circuit of the patient interface or blower (not shown). In some embodiments, temperature control for the heated tube and/or humidifier may be implemented by a control system described in U.S. Provisional Patent Application Nos. 61/034,318 filed on 6 Mar. 2008, 61/042,112 filed on 3 Apr. 2008 and 61/084,366 filed 29 Jul. 2008, the disclosures of which are incorporated herein by reference.

For purposes of regulating the temperature and/or humidity of the breathable gas with the heating elements, the apparatus may also include one or more humidity sensors 117, 121, 136 and/or one or more temperature sensors 115, 118, 119, 132. The sensors generate temperature or humidity signals (illustrated as T(t) and H(t) in FIG. 1) for controlling or setting temperature and/or humidity of the comfort devices. Optionally, some of the sensors may be located for measuring ambient conditions. Thus, these sensors would be located away from the heaters and humidifier chamber so as to provide a more accurate reading of ambient conditions.

Figure 3:
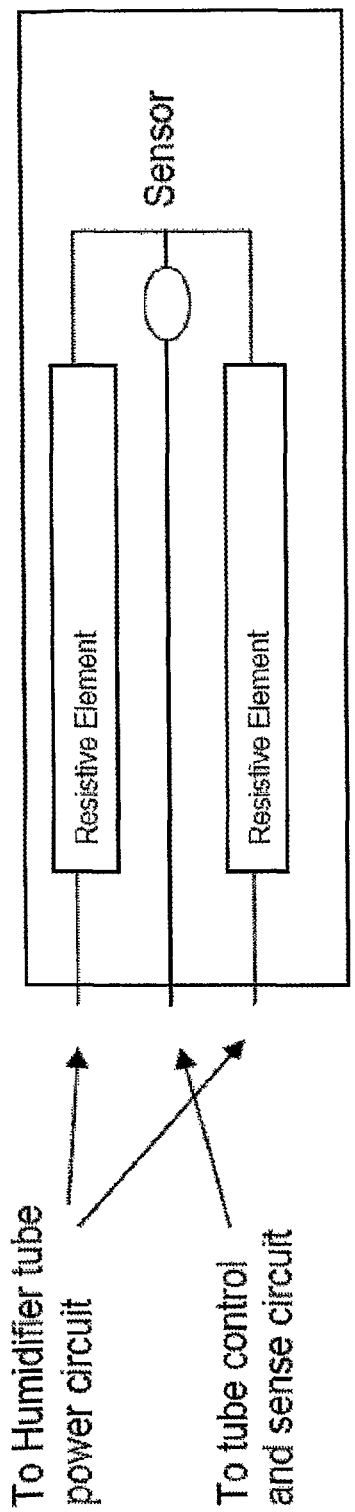
FIG. 3 is a diagram illustrating heating elements of a heated delivery hose.

In some embodiments, the heated tube as previously mentioned may be constructed with three wires embedded therein. Two of the wires may be heating elements designed to warm and transfer heat to the passing breathable gas. The heating wires may optionally be spiraled around and along the delivery tube. The remaining wire may be a sensing wire to allow communications between a temperature sensor coupled with the wire. Such a configuration is illustrated in FIG. 3. The two heating elements may be designed with a loosely balanced bridge that permits the driving circuit to monitor the voltage at the sensor for half of the applied voltage. If the sensed value (voltage or temperature) is not considered a plausible measurement, then the system may indicate a fault. The sensor may be a thermistor located in a cuff of the delivery tube near the patient mask or cannula but in close thermal bond with the air passing through the tube.

The sensor may be a high impedance type that allows detection of the temperature of the air by removing drive voltage to the heater elements and measuring resistive value, taking account of the heater element impedance. The sensing element may be located between the two heater elements.

In some embodiments additional accessory components such as supplemental diagnostic devices may be incorporated with the respiratory treatment apparatus. For example, the apparatus may be equipped with a global access module or GAM. The GAM can provide wireless communications between the GAM module and an external communications system, such as a GPRS Data system or GSM phone network. Such a device can permit communications for modifying operations of the respiratory treatment apparatus or monitoring its operation and data logging from sensors or analysis of the patients' condition (e.g., SDB events). The system may also include a USB interface for external control or data communication with other devices such as a desktop or laptop computer. The system may also include a smart card or other data card interface (e.g., an SD card) for storage of data from the system or updating or changing software or firmware for the control of the respiratory treatment apparatus. Still further, an embodiment of the respiratory treatment apparatus may be equipped with a pulse oximeter for gathering oximetery data about the user of the apparatus.

In some embodiments some or all of the sensors (when present) may be controlled by a controller or processor (not shown), which may be a sensor control processor. In this regard, the sensor control processor may be, for example, an 8 bit R8CV 1A/1B bit device or other digital microprocessor. Optional analog-to-digital (A/D) converters/samplers (not shown separately) may be utilized in the event that supplied signals from the sensors are not in digital form and the sensor control processor is a digital controller. The sensor control processor essentially controls the timing of readings from the various sensors and may communicate sensor signals as a digital message(s) to a system level processor. As discussed in more detail herein, the sensor control processor may be a slave device to a system level processor that provide sensor information in response to request messages from the system level processor.

Thus, in some embodiments some or all of the signals from the various sensors or the sensor control processor (when present) may be sent to a system level controller or processor 120. In this regard, the processor may be an ARM Cortex 32 bit device or other digital microprocessor and may be implemented with a real-time operating system, such as an operating system provided by Green Hills Software or Micrium. Optional analog-to-digital (A/D) converters/samplers (not shown separately) may be utilized in the event that supplied signals from the sensors are not in digital form and a sensor processor is not implemented. Based on input signals or messages from these sensors and/or other optional sensors, the controller may in turn generate control signals or messages such as blower control signals and/or heater and/or humidifier control signals. For example, the controller may generate an RPM request signal to control the speed of the blower 104 by setting a desired frequency or rotational velocity set point and comparing it with the measured condition of a frequency or velocity sensor. Alternatively, such changes may be based on determining a desired pressure set point and comparing it with the measured condition of the pressure sensor. Typically, such changes to the motor speed are accomplished by increasing or decreasing supplied motor current with the servo based on determined differences between set and measured conditions such as in a closed loop feedback fashion and translating the difference to current. Thus, the processor 120 or controller may make controlled changes to the pressure or flow delivered to the patient interface by the blower 104. Optionally, such changes to pressure or flow may be implemented by controlling an exhaust with a mechanical release valve (not shown) to increase or decrease the exhaust while maintaining a relatively constant blower speed. Optionally, the controller may also generate control signals for the other components of the system (e.g., the humidifier, heating elements, communications components, diagnostic devices, data storage components, etc., to adjust the operation of these elements and receive information from them. Similarly, additional control signals or messages may be generated by the system level controller to the other components of the apparatus in the control of these components as discussed in more detail herein.

The system level controller or processor 120 is typically configured and adapted to implement particular control methodology such as the methods and algorithms for power management described in more detail herein. Thus, the system level controller may include integrated chips, a memory and/or processor control instructions or data in an information storage medium. For example, programmed instructions encompassing such a control methodology may be coded on integrated chips in the circuits or memory of the device or such instructions may be loaded as software or firmware using an appropriate medium. With such a controller or processor, the apparatus can be used for many different airway treatment therapies, such as the pressure treatments previously mentioned, by adjusting a pressure delivery equation that is used to set the speed or pressure of the blower or the exhaust venting by the release valve. Thus, flow or pressure may be set to desired levels as set by the switches of the device and optionally increased in response to detected respiratory conditions such as an apnea, hypopnea, obstruction etc. They may also be kept generally constant over the respiratory cycle. Additionally they may provide some end expiratory relief or smoothly change to replicate the patient's detected respiration cycle. For example, a patient's respiratory cycle may be detected by comparing an average pressure signal such as a low pass signal from a pressure sensor with an instantaneous pressure signal from a pressure sensor to determine whether the instantaneous signal exceeds the average signal. When it exceeds the average signal, an inspiratory phase may be detected and an inspiratory pressure level may be delivered by the blower. When the instantaneous signal does not exceed the average signal, an expiratory phase may be detected and an expiratory pressure may be delivered by the blower. Other methods may also be implemented to detect the patient's respiration and may be based on signals from other transducers or sensors such as by monitoring a flow signal from a flow sensor. Similarly, various humidity and/or heating methodologies may also be implemented with the controller such as in accordance with detecting the patient's respiratory cycle. Moreover, changes to these treatment regimes may be made based on detected power conditions of the system as discussed in more detail herein.

The respiratory treatment apparatus will also typically include a power supply unit PSU. Optionally, the power supply unit may be configured to provide 30, 60 and/or 90 watts of power. For example, the power supply apparatus may include a mains power supply component so that the subsystem components of the respiratory treatment apparatus may derive their power from a conventional external power system. For example, the mains power supply may be coupled to an A/C power source (e.g., 240 volts at 50 Hz A/C or 120 volts at 60 hz A/C.) Typically, the power supply unit may also be configured with one or more batteries to power the respiratory treatment apparatus in the absence of an external mains connection. The battery may also include a charger for re-energizing the batteries and a battery regulator to assist with evenly charging the cells of the battery or batteries. Still further, a DC converter may also be provided to permit an external DC source to provide power to the system or charge the batteries when a mains power supply is not available. For example, the DC source may be an automobile battery or automobile outlet. In some embodiments, a fuel cell may optionally serve as part of the power supply unit like the battery described herein.

Figure 4:
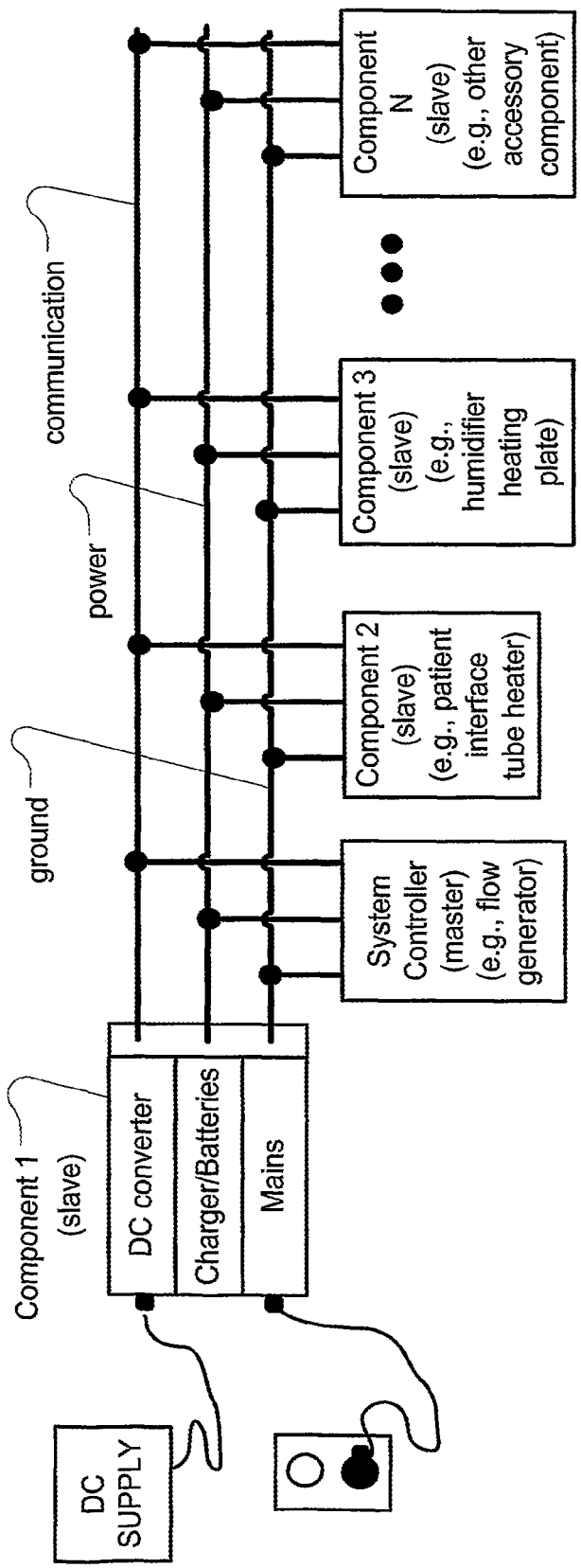
FIG. 4 illustrates an example control bus of the present power management technology suitable for use with the respiratory treatment apparatus of FIG. 1 or 2.

In some embodiments, the system components may be coupled together for electrical communication by a common system bus. An example of such an embodiment is illustrated in FIG. 4. For example, the system bus system may be implemented with a power supply line (e.g., a 24 volt supply line) a communication line (e.g., a 3.3 volt VCC logic high level) and a ground line. Each component of the respiratory treatment apparatus may be coupled to each line of the bus in a multi-drop configuration. In addition, the bus may optionally be configured as an open drain system.

With such a bus, the system level controller may be implemented to command or interrogate any of the components of the bus system (e.g., the flow generator, the delivery tube heater, the humidifier, the power supply, computer interface, diagnostic components, sensor control processor etc.) over the communication line of the bus. The system controller may operate as a master device with the additional components of the bus operating as slave devices. For example, in a half duplex fashion, the system level processor may send commands on the communication line at a low baud rate (e.g., 9600 baud) and receive a response, such as a status message, from the polled component that recognizes the command over the same communication line. The status message may include information regarding the component such as its set mode of operation or data from sensors associated with the particular component, etc. An absence of a response may indicate an error. A suitable message format may be a 10 bit message including one start bit, eight data bits and one stop bit, such as a format defined by EIA-232 standard.

Example command messages may include some illustrated in the following table:

| Command Type | Function |
| --- | --- |
| Synch/null message | Wake from sleep |
| PSU interrogate | Determine PSU type |
| Humidifier Read | Read the temperature of the humidifier heater element |
| Humidifier Set | Set the power level of the humidifier |
| Tube Read | Read the temperature of the tube sensor |
| Tube Set | Set the power level of the heated tube |
| Ambient Read | Read the ambient temperature of the humidifier |
| Humidity Read | Read the ambient humidity of the humidifier sensor |
| Sleep Mode | Set one or all sub-systems to low power mode but continue to monitor messages from the bus. |

For example, if the master device issues a sleep mode command to one or all subsystem components, those components may be powered into a low power mode that reserves power for essential functions. In such a sleep mode, the devices may continue to monitor the bus. For example, in response to a sleep mode command to either or both of the heated delivery tube or humidifier, the heater element(s) may be powered off. However, they may be powered on upon receipt of a synch type wake up message.

Messages on the bus may be confirmed by an error correction and/or validity encoding scheme. For example, the transmitters and receivers of the bus may incorporate cyclic redundancy check (CRC) or other similar data validation circuitry or processing algorithm. In the system, if a message transmitted from the master device fails due to the checksum or CRC, no response may be sent by the slave and the master device may retry the command. Similarly, if a master receives an invalid response, the master may resend the original command that invoked the invalid response. The master device may be configured to retry a certain number of times (e.g., two or three) before utilizing some alternative programming or control that addresses the error or failure of the slave component. A suitable timeout period may be implemented in the master while a response is pending (e.g., 200% of the time necessary for the slave component to receive the command and generate a response).

Accordingly, each component or subsystem of the bus may be configured with its own processor or control circuit to receive and respond to the commands of the system level controller on the bus. By connection with the message line of the bus, the component level controller will then control its particular component in response to the commands of the system controller. Thus, the flow generator, humidifier, delivery tube heater, power supply etc. can have a component level processor or controller. However, in some embodiments, the system level controller may be integrated with any one or more of the system components. For example, the system controller may serve as the component level controller for the flow generator.

For example, the system level controller may generate control messages to a slave component humidifier processor to operate at a certain temperature or humidity level. The humidifier processor or controller will in turn generate control signals to operate the humidifier heater or delivery tube heater as a bang-bang controller. Such a control scheme of the humidifier processor may simply operate to engage or disengage the heaters depending on whether the measured temperature is below a threshold set point temperature or whether power conditions require disengaging these components. However, in some embodiments, the controller may receive temperature measurement signals or messages from the temperature sensors, power level signals or messages from system or component power sensors and/or synchronization control signals or messages from a system level controller, and in turn generate heater control signals based on a more variable control. For example, a proportional integral derivative control methodology or integral control methodology may be implemented to variably adjust the power supplied to operate the heater elements based on a temperature set point or other related system criteria as will be discussed in more detail herein. With such a variable power level control scheme, the heaters may be set to one of several different power operation levels depending on the level of needed increase in temperature. This can permit the heaters to operate more efficiently in conjunction with the remaining components of the system.

In some embodiments, the power supply unit can be implemented with a component level control circuit or processor that permits a master device to detect information about the power supply unit such as the type of power unit or the active source of the unit that is supplying power or the level of power being supplied. Optionally, it may further detect the transient condition of the power supply unit such as available power, discharge rate or condition of a battery. Such a detection implementation can permit the master device to be programmed with different power-wise control strategies based on the connected or operative power supply and/or its condition. For example, upon detection that the power supply is supplying current from a battery of the power supply unit rather than a mains supply, the controller may power down a heating element to a lower power consumption mode or to a sleep mode to reserve energy for more essential systems such as the flow generator. For example, if a battery supply or low power supply is detected, a sleep mode may be issued to some of the components of the respiratory treatment apparatus such as the humidifier or heated delivery tube. Alternatively, or additionally, some of the components of the apparatus may be commanded to change to a lower power operation mode. For example, the humidifier may be set to produce lower humidity or the heating tube may be set to generate heat at a lower temperature. In some embodiments, lower power availability may result in the system controller changing the type of respiratory treatment therapy provided by the apparatus. For example, if a respiratory treatment apparatus is delivering a bi-level CPAP therapy when it detects a reduction in available power (e.g. a drop from 90 watt supply to a 30 watt supply), based on the prioritization programming of the controller, the apparatus may change the bi-level treatment to a less power demanding therapy such as a continuous level of CPAP therapy or an automatically adjusting continuous level of CPAP therapy (e.g., APAP).

This detection of the operation of the power supply may be based on a command message from the master device that requests from the power supply unit as a slave device to identify the source of power or type of power supply unit and/or the condition or availability of power. A response message may be coded with the information for the master device.

Figure 5:
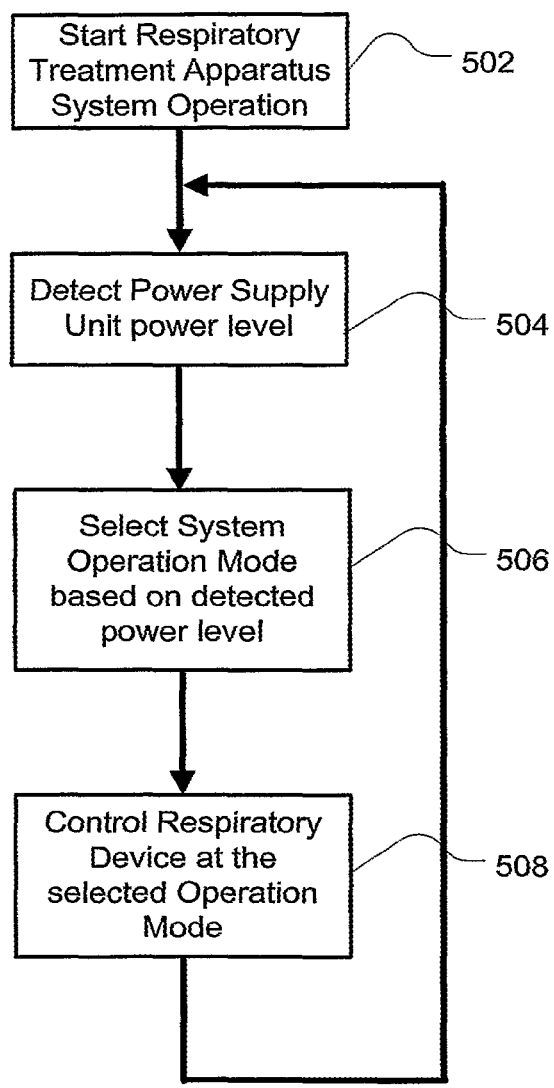
FIG. 5 is a flow chart of a methodology for power management control in an embodiment of the respiratory treatment apparatus.

A process embodying an example of the power-wise control of the respiratory treatment apparatus is illustrated in FIG. 5. At 502, the respiratory treatment apparatus starts operation. At 504, a power supply condition is detected. This may be based on a messaging from the system level controller to the power supply unit. At 506, the system level controller sets operation based on the power information provided by the power supply unit. For example, if a low supply condition is identified, a therapy control algorithm may be changed (e.g., from a bi-level treatment to an approximately constant level treatment). Optionally, large power consumers such as heater or humidifier components may be disengaged or changed to a low power consumption mode where lower temperatures are maintained. At 508, the respiratory treatment apparatus is controlled at the modified treatment methodology. After 508 flow may return to 504 to detect the power condition. If a normal power level is detected, the treatment regime may then be returned to the prior regime in 506 and 508 as it was prior to the detection of the low power condition.

Figure 6:
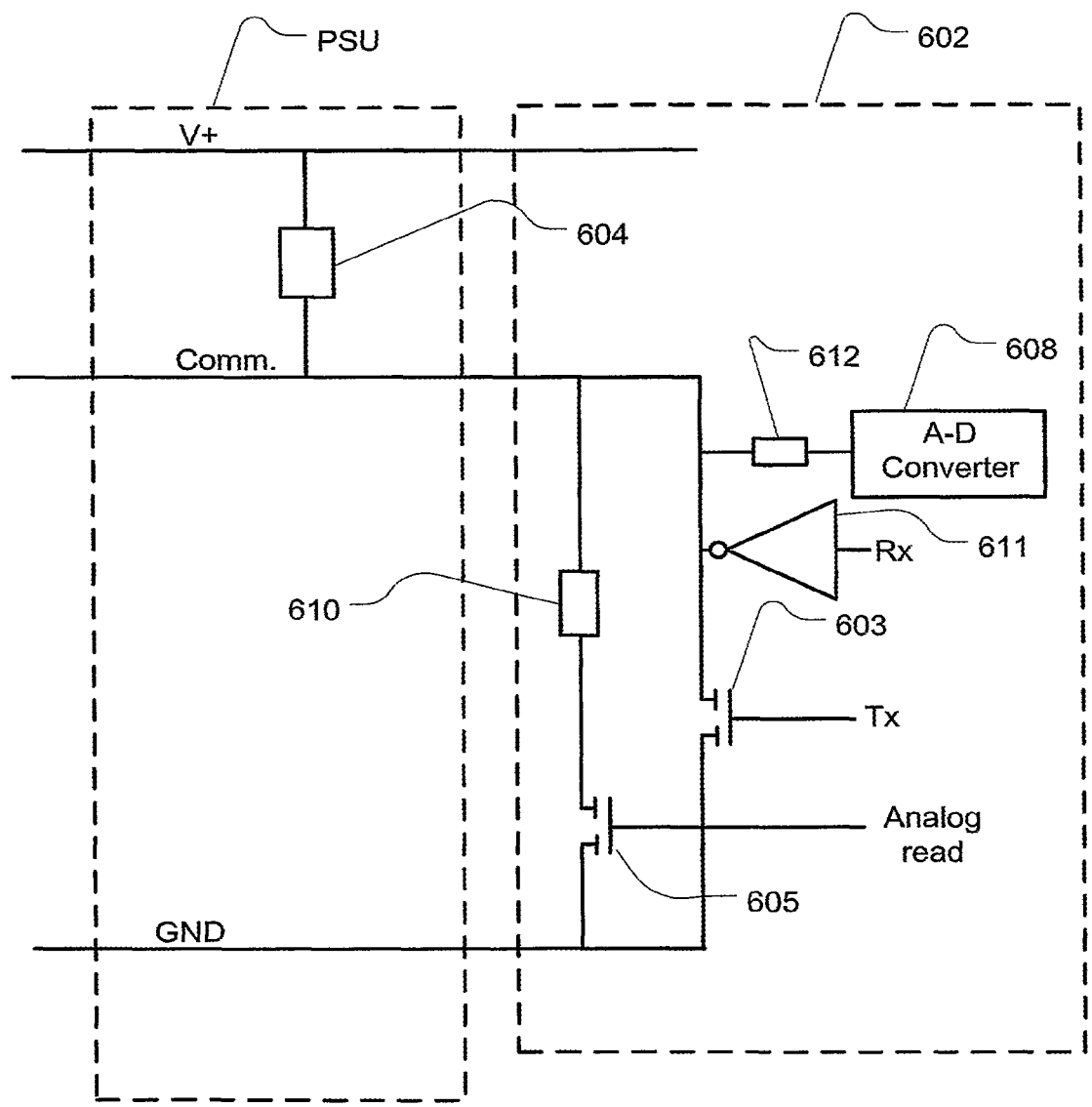
FIG. 6 illustrates an example connection between a power supply and a bus transceiver component suitable for use with the respiratory treatment apparatus of the present technology.

In some embodiments, the power supply information for power-wise operations may be detected by components of the system that implement an analog detection circuit as illustrated in FIG. 6. The testing of the supply level may be programmed into the system controller to take place at regular intervals during operation (e.g., every five minutes or less) so that the controller can set system operations based on changes in the power supply unit during operation.

FIG. 6 illustrates a transceiver device 602 suitable for analog and digital sensing of the communication line of the open collector bus illustrated in FIG. 4. The transceiver device 602 may be implemented in a master or slave component of the bus. For example, the transceiver device 602 may be implemented as a transceiver for the power supply unit or a system level processor. The receiver element of the device may sample the voltage of the communication line of the bus via the receiver component (shown as RX) for receiving messages of the bus, which may optionally utilize an inverter 611 such as if opposite logic levels are used for the transmit and receive signals of the bus. Similarly, the transmission element (shown as TX) of the device may modulate the voltage of the communication line of the bus for transmitting messages on the bus by activating the transistor element 603. During transmission and reception of digital signals on the communication line of the bus, the analog read element (shown as Analog Read) is left inactive.

Optionally, a pull up resistor 604 may be implemented to code information about a component coupled with the bus such that different resistors may indicate different components or different component functionality. In this illustrated example of FIG. 6, the encoded component is the power supply unit (PSU). The resistor value may be sensed by other components of the bus, such as by the transceiver 602 of a system level controller component. To this end, the analog sensing elements of the transceiver 602 may determine the value of pull up resistor 604. Optionally, resistor 604 may be implemented with two or more resistors as a Thevinin equivalent, for example, in the event that the communications bus utilizes a different voltage level. In this device detection mode, the TX and RX elements are left inactive. The analog read transistor 605 is asserted (closed) to place an analog voltage value on the communication line of the bus. A known analog sense resistor 610 may be utilized as part of the resulting voltage divider circuit to permit a determination of the voltage on the bus associated with the pull-up resistor. The voltage value may be detected by the analog to digital converter 608. A protection resistor 612 may be utilized to protect the A-D converter.

For example, if the pull-up resistor represents the type of power supply, a detection of 3.9 K ohms may be interpreted by a master controller that the power supply is an infinite supply (mains). A detection of 2.7K ohms may be interpreted as a 90 Watt power supply. A detection of 1.8K ohms may be interpreted as a 60 Watt power supply. A detection of 1.0K ohms may be interpreted as a 30 Watt power supply. Other voltage levels and coding schemes may also be utilized to code information about the power supply unit in this analog manner. Optionally, digital messaging may also be utilized to detect information about the power supply unit or other components of the bus. In such a case, a data message with information from circuits or memory of the power supply unit or based on signals from the detectors or sensors of the power supply unit may be sent from a processor of the power supply unit to a system level controller or processor.

With respect to further power-wise control or operations, the apparatus or power supply unit may also include sensors for detecting information about the performance or condition of the power supply unit such as power availability of a battery. Such a power condition sensor or detector may be implemented with a temperature sensor (e.g., thermocouple, thermo sensor or digital thermometer—illustrated in FIG. 1 as temperature sensor 140), power or current sensor (illustrated in FIG. 1 as power or current sensor 142), and/or a timer. For example, in some situations, a battery may be able to provide peak current in excess of its average current rating for a short period of time without harming the battery. Such an overload condition of the battery may be utilized for short term operations of the respiratory treatment apparatus that may require more power than the battery is capable of providing on average. With the sensor(s), power, current, temperature and/or time data may be utilized as one or more indicators that permit the battery to operate at peak or overload performance conditions for a short period. For example, peak or overload battery performance conditions (e.g., peak power or peak current) may be utilized to provide power to heaters of the apparatus or other accessories during a brief warm up period when rapid warming/humidification of the treatment air and/or of the patient interface tube(s) is desired. To ensure that the peak battery operation condition does not also harm the battery, the sensor(s) can provide information to the system controller to indicate when the peak operation should be discontinued or that peak operation is or is not permissible. For example, if the duration of an operation associated with peak or overload power use of the battery exceeds a time threshold and/or if operational temperature of the battery exceeds a temperature threshold, these conditions can serve as a trigger in the apparatus to prevent initiation of or discontinue the overload battery operation condition. Such a system design can safely permit use of batteries having lower average power specifications while still meeting short term peak power demands in the operation of the respiratory treatment apparatus. Thus, smaller power supply and/or smaller batteries may be implemented. This may help to reduce apparatus size and/or to reduce the cost of the apparatus.

Optionally, the power supply unit may be configured to provide a system level controller with data to identify the amount of power available for an overload or peak operation and/or the amount of time that the overload condition may be safely operated so that the processor of the system level controller may use the data in controlling the system based on the overload condition. In such a situation, the controller may simply limit its use of power at the overload condition levels to the specified time period and discontinue them thereafter for a predetermined period of time before doing so again.

Additionally, a temperature sensor proximate to the battery cells or power supply unit as just described may be utilized to provide the system level processor or controller with information about an overheat situation of the power supply unit and/or battery. In response to an indicator of an undesirable heat level, for example, if a temperature signal or data from a temperature sensor exceeds a threshold, based on a system level processor comparison, the system level processor may be triggered to change its operation or treatment regime to one with a lower power consumption characteristics compared to a formerly provided treatment regime. Such an operation can permit the apparatus to protect its battery from damage due to overheating, for example, if the power supply unit or apparatus is inadvertently covered by a blanket of a patient using the apparatus in a manner that causes the power supply unit to trap rather then vent heat.

Optionally, when a power supply unit condition sensor(s) of the apparatus is implemented with a power sensor, current sensor, amp meter or the like, the sensor can provide power information to a processor of the system. For example, instantaneous current discharged from the battery may be monitored or measured over time. A processor of the system may track the current or power (e.g., average power etc.) and compare the expended or measured values to expected values such as the expected values defined by specifications for the batteries of the power supply unit and stored in memory of a processor of the system. This can permit the processor to determine remaining power available for a particular period of time with a battery. If a comparison(s) based on the remaining available power indicates a shortage of power with respect to the power that is required for a present therapy regime being provided by the device then therapy control operations may be adjusted to compensate for the available power conditions as previously discussed. Thus, a system level controller or processor can be programmed to implement power-wise control decisions, such as those previously described, with information from the power-related sensor(s) during battery operations.

Thus, in some embodiments, a processor or controller circuit associated with a battery may store data parameters, such as in a memory, that represent information regarding the power supply unit, such as information regarding the charging of the battery. By way of further example, one or more processors of the apparatus may store or access data to determine such information as (1) how much charge the battery has (e.g., a percentage), (2) how much charge the battery needs (e.g., a percentage), (3) the time the battery needs to charge to be complete, (4) the time that the battery has been charging, (5) the charging mode that the battery has been charged in, (6) how many hours are available for treatment with the battery, (7) energy consumption information such as cost of the energy use and/or charging costs, (8) battery life and cycle usage information, (9) replace battery information such as battery performance degradation, (10) failure of the mains supply (e.g., power outage) including, e.g., dates and/or times of outages, etc. This data may be for a current treatment session (e.g., a night's use) and may also be included for prior treatment sessions so as to provide historic power supply data. Thus, in some embodiments, stored historic data of battery usage, charging, power, etc. for one or more prior treatment sessions may be utilized in subsequent treatment sessions.

Accordingly, many power-wise control strategies involving the methodology illustrated in FIG. 5 may be implemented. By way for further example, in some embodiments, the apparatus may monitor average power consumption or discharge rate of the power supply unit, such as after detecting that the battery is providing power to the device. The processor may also monitor the time that the apparatus has operated from start of a particular treatment session with the apparatus and/or start of using the battery. The processor then may determine the likely remaining time of use of the device such as with an internal clock or timer and a measure of the remaining available power for that period. The processor of the apparatus may then modify the therapy regime such as the pressure or flow from the flow generator and heating/humidification settings of the accessories to ensure that sufficient power would exist to continue to provide some therapy for the expected duration of the session before expending all power of the battery of the power supply unit based on its discharge rate and specification.

For example, in some embodiments, the processor may include or access data or formulas representative of the power consumption requirements of the different accessories at different settings over time. In such an embodiment, the apparatus may include data representing the power consumption requirements of the flow generator to generate a bi-level flow and a constant level of flow for a period of time at various pressure levels. Similarly, the apparatus may include data representing power consumption requirements of operating a humidifier at various temperatures and data representing power consumption requirements of operating one or more tube heaters at various temperatures for a period of time. Based on measurements or determinations of remaining available power and/or a determined discharge rate from the batteries of the power supply unit, the processor of the apparatus may then determine or select a therapy regime that can last for the duration of the expected treatment session. Thus, the algorithms of the device may automatically select a heat setting, humidification setting and/or flow setting based on the stored power consumption requirements and detected available power to permit the apparatus to consume power during the remaining session in a manner that avoids depleting all of the power of the batteries.

For example, the controller or processor may select a bi-level pressure or flow treatment, high heat and high humidity settings for both the start of a treatment session and/or the end of a treatment session when the patient is most likely to be awake such as, for example, the first half hour and last half hour of a typical sleep session (e.g., seven or eight hours). However, the apparatus may select lower settings during the interim sleep period of the treatment session when the patient is most likely asleep. Thus, lower heat and humidity settings may be controlled by a processor of the apparatus during this interim time period to reduce power consumption. Additionally, a substantially constant pressure treatment level rather than a bi-level treatment may be delivered by the flow generator during the interim period to conserve power based on the determination of available power. Alternatively, in some embodiments, such a therapy regime as just described may be preprogrammed to occur simply upon activation of battery operation and discontinuing of use of a mains power supply rather than being based on an automated determination of remaining available power. Optionally, for a treatment apparatus that automatically detects sleep events such as apnea, hypopnea or obstruction and then automatically adjusts treatment pressure to treat the events, the flow generator may continue to make such automated pressure changes in response to these events or an absence of these events during the interim period of the session. Alternatively, the processor may also determine based on the available power or discharge rate that the automatic detection of such events and pressure changes should be discontinued to permit the flow generator to continue to provide some treatment to the end of the sleep session given available power. The processor of the apparatus may periodically revise the treatment regime based on periodic evaluations of available power and discharge rate of the batteries and the power requirements of the components of the apparatus as the available power or discharge rate changes over the treatment session.

Optionally, the changes to the power consumption of the components of the apparatus may be prioritized such that the operation of less necessary components may be modified to reduce power before other components. For example, a heater may be switched to a lower power operation mode while the flow generator continues at a typical power operation mode because the heater may have lower prioritization indicia in the algorithm of the processor compared to higher prioritization indicia of the flow generator. Thus, if remaining power permits, changes to the therapy regime made by the processor may avoid changes to the pressure treatment regime provided by the flow generator but allow changes to temperature settings of heating elements of the apparatus.

In some embodiments, the algorithms or circuits of the processor may control changes to the provided therapy by using energy profiles that are each associated with different treatment regimes. A profile may include data stored in a memory of the apparatus that represents energy information for operation of a group of components (e.g., a flow generator, heater and humidifier) at particular settings with respect to time (e.g., a measure representative of power or a measure representative of current use with respect to time). Optionally, each profile may include information for a single component such that it identifies energy information for operation of that single component at particular settings. Many profiles may be included. The data of the profiles may be preprogrammed into the apparatus. However, the profiles may optionally be modified over time by a processor of the apparatus based on measured power consumption conditions during actual use of the particular profile with the apparatus and a particular patient. Thus, a processor may update energy profiles such as by updating an average current or power consumption rate at particular settings for the component(s) of a profile. Changes to the treatment regime based on the detection of a discharge rate or average discharge rate and a determination of an expected remaining time of the treatment session may then be implemented by an evaluation and/or selection of one or more of several energy profiles. The system level processor of the apparatus may then control the operation of the apparatus according to the modes of operation indicated by the one or more of the selected profiles. Thus, energy profiles may quantify the power consumption of different modes of operation of different components of the apparatus to permit a processor to select a mode of operation based on the quantification to stay within measured or otherwise determined remaining available power. Optionally, the profiles may also include prioritization indicia to also prioritize certain components over others based on patient needs. For example, the profiles may also indicate that higher heat settings may be discontinued or adjusted before changing a pressure treatment regime depending on the detection of available power.

For example, a flow generator of the apparatus may be characterized by multiple profiles. In such an embodiment, one profile may characterize a bi-level pressure treatment regime that has a particular rise time by data representing its energy consumption rate during battery operation for one or more pressure levels. Another such profile may characterize a similar bi-level pressure treatment regime but where the bi-level adjustments utilize a different or slower rise time between expiration and inspiration such that the latter profile has data indicating that it has a lower energy consumption rate for the one or more pressure levels. Thus, a processor of the apparatus may determine power availability for a remainder of a treatment session, such as by monitoring a battery current discharge for a period of time and determining a measure of the remaining energy that will be available for the remainder of the treatment session. The determination of remaining power may be based on specification of the battery or historic use information recorded by the apparatus. The processor may then select the latter profile rather that the first profile to reduce power consumption to preserve power if the energy requirements of the latter profile meet the determined available power reserve and the energy requirements of the former profile can not be satisfied by the available power reserve. Such a determination under the control of the controller or processor can permit the apparatus to continue to provide treatment during a remainder of an expected treatment session (e.g., the remaining time for a typical sleep session) by using the most desired treatment regime as defined by the different profiles.

In some examples of the technology, an estimate of the power needed for an expected remainder of a treatment session (e.g., the remaining time for a typical sleep session) may be based on stored historic treatment session information recorded by the device during use by the patient. Such historic information may be, for example, the power used during certain time periods of a prior treatment session and/or total power used in a prior treatment session and/or an average from several prior treatment sessions. Remaining or expected treatment session time may similarly be based on one or more prior treatment session times or an average thereof.

Still further, the profiles may also indicate different timing priorities depending on the particular time within a treatment session. For example, a certain heat and/or certain humidification setting may have a lower priority during the middle time period of a treatment session but a higher priority during a beginning and/or ending portion of the treatment session. Such an implementation can permit the processor to conserve energy when a patient is asleep and less aware of the treatment, for example, by avoiding controlling high heat with the heating elements when the patient is asleep. The controller could then utilize that energy with the heating elements to generate high heat when the patient is more likely to be awake and more likely to desire that particular treatment.

In some embodiments, one or more components (e.g., the humidifier, delivery tube heater, flow generator etc.) of the system may be provided with power supply sensors to detect the power conditions of the systems or components. For example, the analog sense elements of the transceiver 602 circuit may be implemented to detect whether available system or component voltage associated with the supply voltage line (V+) falls below a threshold voltage level. If the voltage condition falls below the threshold, one or more components may be powered down to a lower operating voltage condition or a zero voltage condition to permit available power to be utilized for other components of the system. With such power sensors, one or more threshold conditions may be detected to permit different power down conditions for different components so as to permit less important components to power down sooner than more important components. Such a sensor may be implemented as a component specific sensor in a component level controller to power down the component configured with the sensor in a manner that is independent of the system level controller of the respiratory treatment apparatus. Alternatively, one or more such sensor(s) may provide power information to a system level controller. The system level controller may in turn prioritize the power adjustments to the components based on a power prioritization module or algorithm associated with the system level controller. For example, with the algorithm or module, the flow generator may be characterized as having a higher priority than the heater elements of the system. Similarly, the humidifier may have a higher priority than the delivery tube. The system level controller may then send messages to the components of the bus to power down or change operations of the components based on the prioritization scheme.

In one power management method, the flow generator may monitor use of the mask or patient interface. If the flow generator detects that the device is not in use or dislodged, for example, due to detecting a drop in mask pressure below a threshold or below a threshold for a certain period of time, the system level controller may disengage accessory components or otherwise put them in a low power sleep mode to preserve power. This may include, for example, the heating elements, humidifier or heated tube and/or the flow generator itself. These may be re-engaged for operation if reactivated by the user by the controls of the apparatus. However, in the event that the flow generator has not been powered down, the accessory components may be reengaged for operation if a measure of mask pressure returns to a normal level above a suitable pressure threshold.

By way of further example, in some embodiments the power source may be controlled to provide a battery power boost to the system in combination with another power supply of the system, such as a mains supply, depending on the detected conditions of the system. For example, an automated detection of an apnea may control an increase in provided power so as to permit an increase in pressure delivered by the flow generator. In such an embodiment, in response to a detection of an apnea condition or other detected respiratory occurrence (e.g., obstruction, flow flattening, flow limitation, etc.), a battery may be switched to a supply or drain mode from a charge or stand-by mode for a period of time to allow the battery to provide supplemental energy support for a component of the system such as the flow generator. In such a case, the power of a mains supply may be joined by the peak power of the battery for a predetermined period of time based on the detection logic and power management logic of the controller to meet the energy needs of the apparatus.

In some embodiments of the technology, different charging modes may be implemented to reduce electricity costs of the operation of the apparatus. For example, in cases where electrical usage costs are different for different times of the day, the apparatus may automatically implement different battery charge modes at different times of the day to reduce these costs. Such a device may be implemented by a charger that may serve as a speed charger and trickle charger. For example, based on a system clock and predetermined or recorded time data, the apparatus may control a trickle charge mode that draws lower current at more expensive times of the day. The apparatus may also control a fast charge mode to charge the battery by drawing higher current at other times of the day.

In some embodiments, the apparatus may also be equipped with a solar panel to generate power to charge the batteries. Similarly a wind turbine, such as a small impeller and generator configured to rotate on exhaust flow from an exhaust port of the system (e.g., exhaled air during patient expiration) may be implemented with the power supply unit to generate power to charge the batteries.

In some embodiments, components or slaves of the bus system may implement messaging as a safety protocol in the event of failure of the master device or system controller. For example, each slave device may operate based on a command message received by the master device. However, if the command is not refreshed after a given set period of time, the slave device may power down. For example, the delivery tube heater or the humidifier components may be configured with control methodology that operates based on the receipt of a command to set a certain temperature. However, the component level controller of these components may be configured to power down if the command is not received again after a certain period of time (e.g., 1 minute). Control with this type of operational timeout period may be implemented in the humidifier, flow generator, heated tube or any of the other accessory components of the apparatus.

Figure 7:
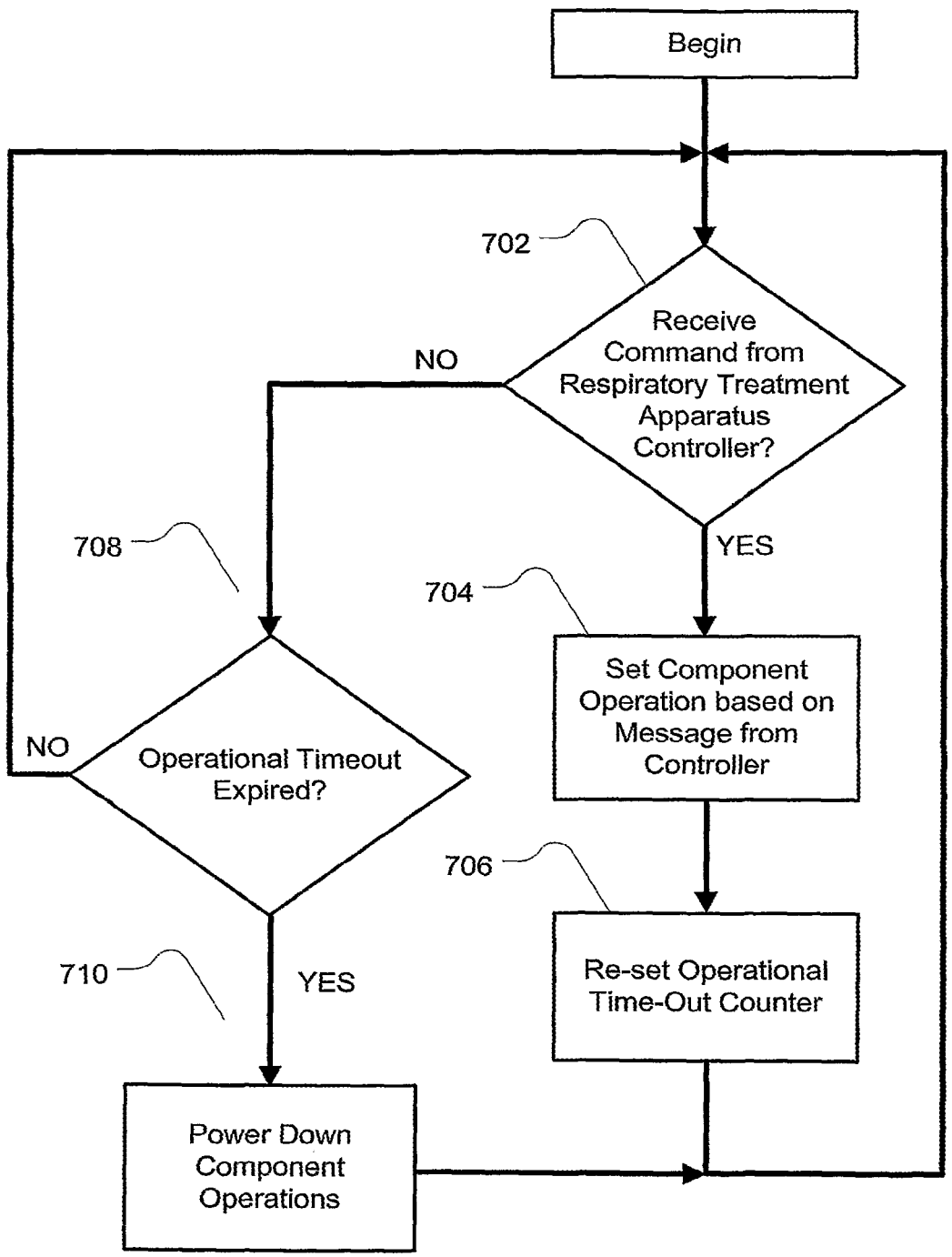
FIG. 7 is a further example flow chart for a power management methodology for an apparatus of the present technology.

An example flow chart for such a methodology is illustrated in FIG. 7. In 702, the component monitors the bus and determines whether a message is received for the slave component. If a message is received for the component, in 704, the component sets or continues operations based on the message received from the master device. Flow moves to 706 where an operational time-out counter is reset. Flow then returns to 702.

If in 702 there is no present message, flow proceeds to 708. In 708, the operational time-out counter is checked to see if it has expired. If it has not expired, flow returns to 702 to check for a message on the bus. If in 708 the operational time-out counter has expired, flow proceeds to 710. In 710, the component is powered down, or placed into a sleep mode or if it is already in that mode, it will remain in that mode. Optionally, if in a sleep mode, control may return to 702 to continue to monitor the bus for further messages.

In some embodiments, the components may be operated by a pulse width modulation control methodology. For example, in setting the operation of one or more heating elements of the system either with a system level processor and/or the component level processor, a processor may generate pulse width modulation control signals. In such a scheme, the duty cycle of the pulse width modulated control signal can be used to set a variable level of voltage for the heating element. For example, a larger or smaller percentage of the duty cycle of the control signal may result in a larger or smaller voltage level being applied to the heating element.

Such a control methodology may be implemented to improve operating efficiencies in the presence of smaller or limited power source levels. For example, in order to avoid peak power operation of multiple heating elements due to a simultaneous current draw situation, operation of two or more of the heating elements of the respiratory treatment apparatus may be interleaved. For example, an interleaving scheme based on pulse width modulation control can be implemented to apply current to different heating elements at different times to avoid simultaneous peak current or simultaneous power draw from a shared power supply unit. Moreover, if the frequency of the PWM control signal(s) are sufficiently frequent, the heating elements controlled by the signals can effectively produce heat concurrently without drawing current (or power) concurrently. Such a control scheme can be applied to one or more of the slave components or accessory devices of the system, such as the humidifier, delivery tube heater, flow generator, system sensors, etc.

Figure 8:
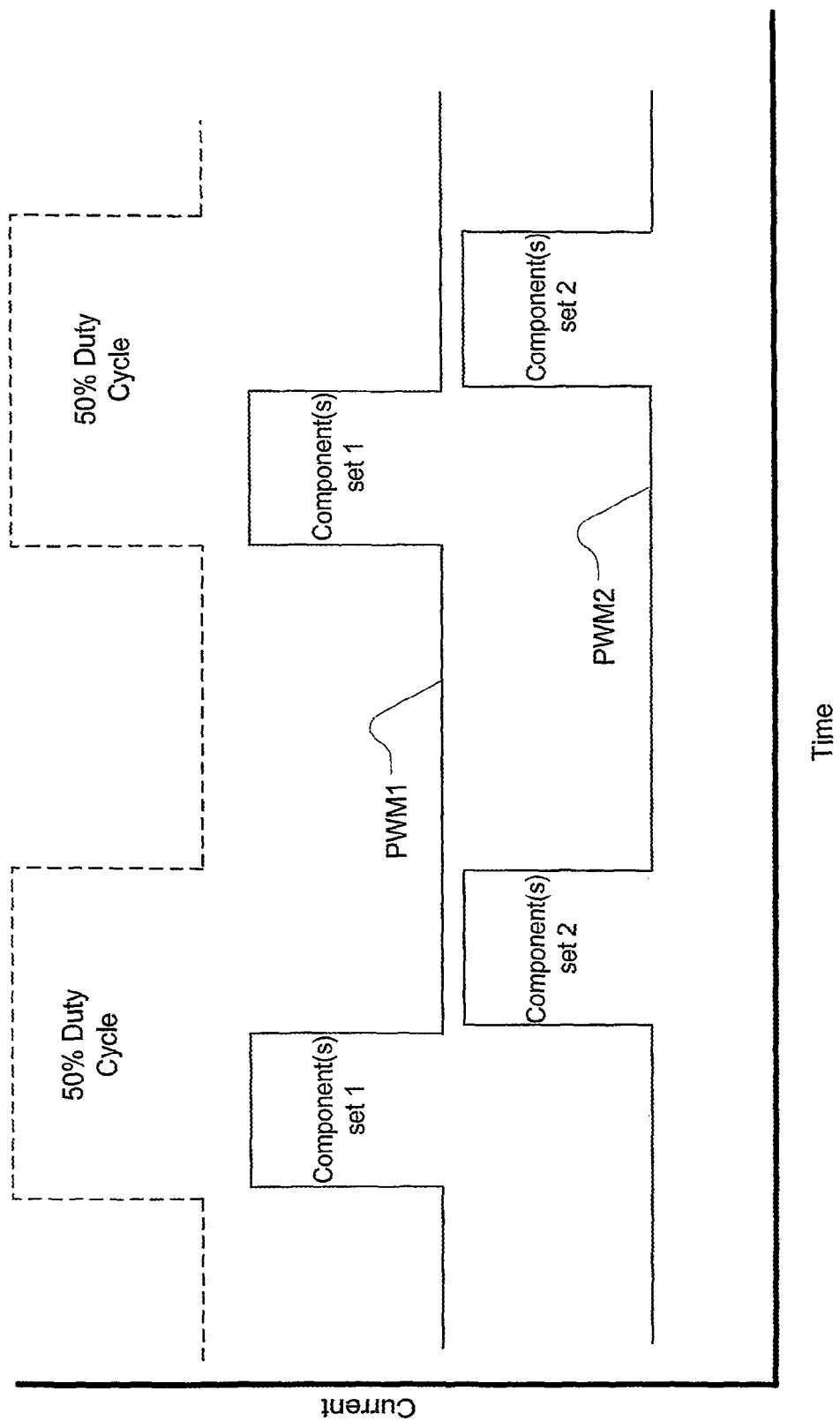
FIG. 8 is a signaling graph illustrating interleaved control of components of a respiratory treatment apparatus of the present technology utilizing pulse width modulated signals.

An example pulse width modulation signal for two interleaved components or accessory devices is illustrated in the signal graph of FIG. 8. In the example, a processor may synchronize generation of first and second pulse width modulation signals (shown as PWM1 and PWM2). This may be accomplished, for example, by utilizing different portions of the duty cycle to divide or share the available power supply. In the example, a first portion of the duty cycle powers a first component(s) set and a second portion of the duty cycle powers a second component(s) set. For example, the first set may include one or more heating elements and the second set may include one or more different heating elements from the first set. In this way, the duty cycle of the apparatus may be divided between different sets in an interleaved fashion to prevent simultaneous power consumption between the sets. In one embodiment of the technology, one or more heating elements of a heated delivery tube may be in one set that may utilized and one or more heating elements of a humidifier may be in another set. In this regard, the processor may be configured to generate the pulse width modulation signals to vary the timing for interleaving purposes. Moreover, the processor(s) that generates the PWM signals may also be configured to modify the percentage of the duty cycle for each set depending on a desired operation of the controlled set of components. For example, in a start up mode for a heating element, a longer duty cycle may be utilized for each set to more rapidly warm up the heating element. It will be understood that although only two sets are illustrated in FIG. 8, additional sets may also be interleaved with additional signals. Furthermore, it will be understood that other signaling schemes may be used to implement interleaving or the mutually exclusive operation between sets of components as discussed herein.

Other interleaving schemes may also be implemented to reduce peak power situations with respect to other components of the respiratory treatment apparatus. For example, there may be certain operations in a flow generator that require more power. In some therapy regimes, a ramping up of pressure may be required during operations depending on the delivered therapy of the respiratory treatment device. Such a ramping or increase may be triggered with the expected or detected start of the inspiratory phase of a patient's respiratory cycle. Sudden increases in the pressure or flow may require an increase in current or power for the flow generator such as in the case where the flow generator increases blower motor speed (RPM) to generate the increase in pressure. Thus, in some embodiments of the present technology, power management may take into account the peak power operations of the blower like the ramping of the motor speed such as with an inspiratory phase related pressure or flow increase. During these operations other devices, such as the humidifier or delivery tube heater, may not be actively powered or may be powered at a reduced level to ensure that peak power of the power supply unit is available for the flow generator. In another embodiment, the operation of the other devices such as humidifiers and heated tubes may be off (not supplied power) or set to a reduced power mode for the whole time of the inspiratory portion of the breathing cycle, not just during the ramping in motor speed for the inspiratory pressure increase, and set on or higher during the expiratory portion of the breathing cycle. In this way, the methodology of the system controller implements a higher power use priority for the flow generator than other accessory components such as the heating elements or humidifier. This may be accomplished by powering one or more of the accessory devices, such as the humidifier and/or delivery tube heater, as a function of a detected respiratory cycle associated with the therapy regime.

Figure 9:
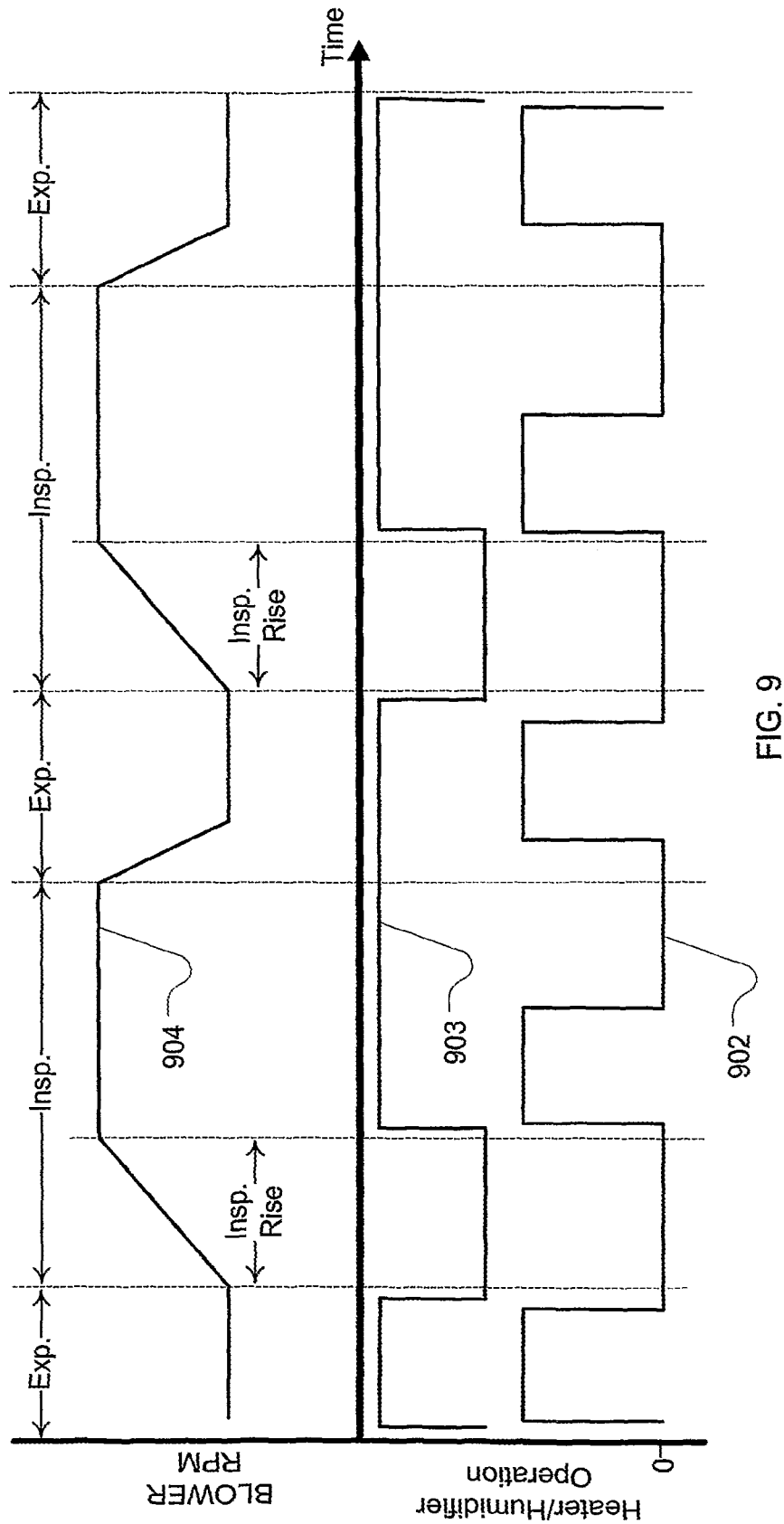
FIG. 9 is a signal graph illustrating interleaving of an operation of humidification and/or heating elements with respect to a portion of a respiratory cycle in the power management control of a respiratory treatment device of the present technology.

An example of such a power management control methodology relating to the flow generator is illustrated in FIG. 9. In the example, pulse width modulation control may be implemented to interleave operations to reduce power of other components or accessories of the respiratory treatment device as a function of the respiratory cycle of the flow generator that may be detected from a patient flow signal or cycled according to the timing of the respiratory treatment device.

FIG. 9 shows a pulse width modulation control signal 902 and a synchronization signal 903 that may be utilized to operate one or more accessories of the apparatus such as the delivery tube heater and/or the humidifier. The signals may be generated by a processor of the device such as the system level processor. The synchronization signal 902 prevents a current draw by one or more heating elements of the delivery tube and/or humidifier during the inspiratory cycle of the flow generator. Thus, the power of the power supply unit will be ensured for an increase in the flow generator illustrated by RPM signal 904. For example, the system level controller may enter an inspiration phase by determining when a measured mask pressure signal (P(t)) falls below an measured average pressure signal (Pave(t)). This triggering in the inspiratory phase may further be utilized to time the generation of the synchronization signal 903 to prevent the accessory device power consumption during the inspiration phase. Logic circuits of the accessory components may then utilize the synchronization signal 903 to govern their operations out of time with particular portions of the respiratory cycle. Optionally, the timing of the synchronization signal may be generated with messaging from the system level controller to the accessory components.

In the example of FIG. 9, the power is interleaved between the flow generator and the heating elements of a humidifier and/or delivery tube heater during the inspiratory rise of the pressure of the blower. While the latter elements are operated during other portions of the inspiratory cycle of the apparatus in the illustrated embodiment, in other embodiments, the operations of accessory components (e.g., heating elements and/or humidifier) may be interleaved during the whole of an inspiratory cycle of the machine. In such an embodiment, the accessory components may only operate or consume current or peak current during the expiratory portions of the respiratory cycle of the machine. In still further embodiments, the interleaving between the flow generator inspiration period and the heating elements as herein discussed may be combined with interleaving between distinct sets of heating elements as previously discussed to result in still further power efficiencies. In such an embodiment, the distinct sets of heating elements are interleaved but neither are operated during portions of the inspiration phase of the respiratory treatment apparatus.

In one embodiment of the respiratory treatment apparatus, blower momentum may be utilized to recharge batteries of a power supply unit of the apparatus. For example, during an expiratory portion of a respiratory cycle of the apparatus, the pressure or flow provided by a blower of the flow generator may be reduced in certain therapy regimes that may be controlled by the device (e.g., a bi-level CPAP therapy). During the reduction from a peak pressure or flow to a lower pressure or flow, the blower may serve as an electric generator. Current from the rotation of the blower motor during that ramp down phase may be fed to the power supply to charge the batteries. This coincides with a deceleration of the operation of the flow generator.

Figure 10:
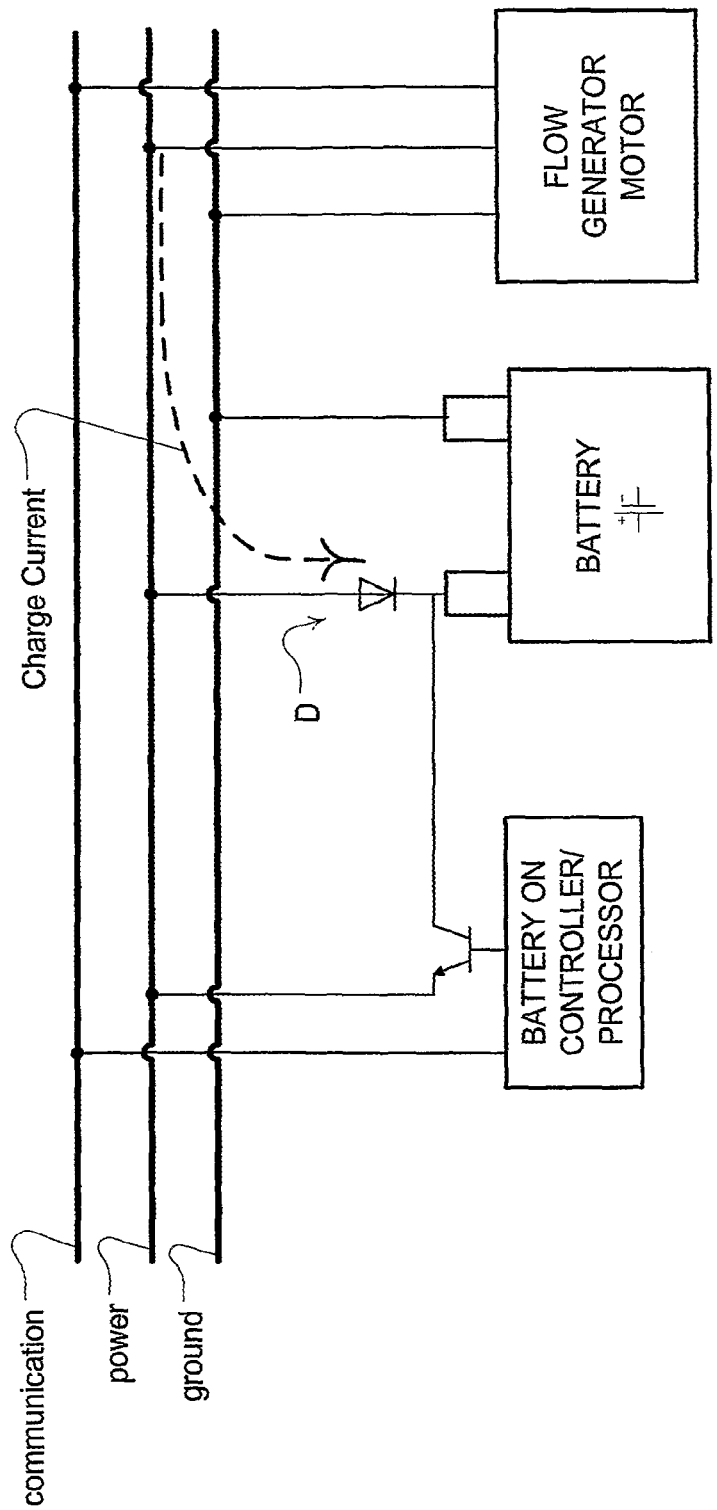
FIG. 10 is a diagram of an example embodiment to charge a power supply unit based on excess current generated from an accessory component or flow generator of the respiratory treatment apparatus.

An example embodiment suitable for recharging the power supply unit is illustrated in FIG. 10. In the embodiment of FIG. 10, the battery is coupled with a bus of the type previously described to permit excess current of the flow generator, such as when the flow generator is decelerating, to charge the battery. It will be understood that the power supply unit associated with the battery will typically also include a mains charger for the battery as previously disclosed. However, such components have not been shown in FIG. 10 to more readily illustrate these principles of the example embodiment. In this embodiment, a diode D may be implemented to permit excess current on the bus to charge the battery. Other circuits may also be implemented to permit excess current on the bus to charge the battery, such as when the flow generator is decelerating. For example, switches may be controlled by a processor of the apparatus to route excess current to the battery when a processor controls a change from an inspiration pressure level to expiration pressure level. In such an embodiment, one or more transistors may permit a flow of excess current from the bus or flow generator to the battery at the end of the inspiration cycle of the device. The transistor(s) may then be switched off to prevent the flow of current to the battery during inspiration. In such a manner, processor control of the charging of the battery may be implemented to gate the excess flow generator energy to the battery as a function of a respiratory cycle of the patient as detected by the apparatus in the provision of pressure treatment such as by monitoring changes in a respiratory flow signal.

Embodiments of the present technology may be configured or programmed so that that power related information, such as the stored parameters, may be displayed to the user in a report on a display of the apparatus or via a data transfer to another device such as a computer. For example, the apparatus may output data such as (1) how much charge the battery has (e.g., a percentage), (2) how much charge the battery needs (e.g., a percentage), (3) the time the battery needs to charge to be full or complete, (4) the time that the battery has been charging, (5) the charging mode that the battery has been charged in, (6) how many hours are available for treatment with the battery, (7) energy consumption information such as cost of the energy use and/or charging costs, (8) battery life and cycle usage information, (9) replace battery information such as battery performance degradation, (10) reliability and/or failure of the mains supply (e.g., power outage) including, e.g., dates and/or times of outages, (11) whether, what and when changes in treatment therapy were implemented as a result of power deficiencies, (12) battery maintenance needs, etc.

Figure 11:
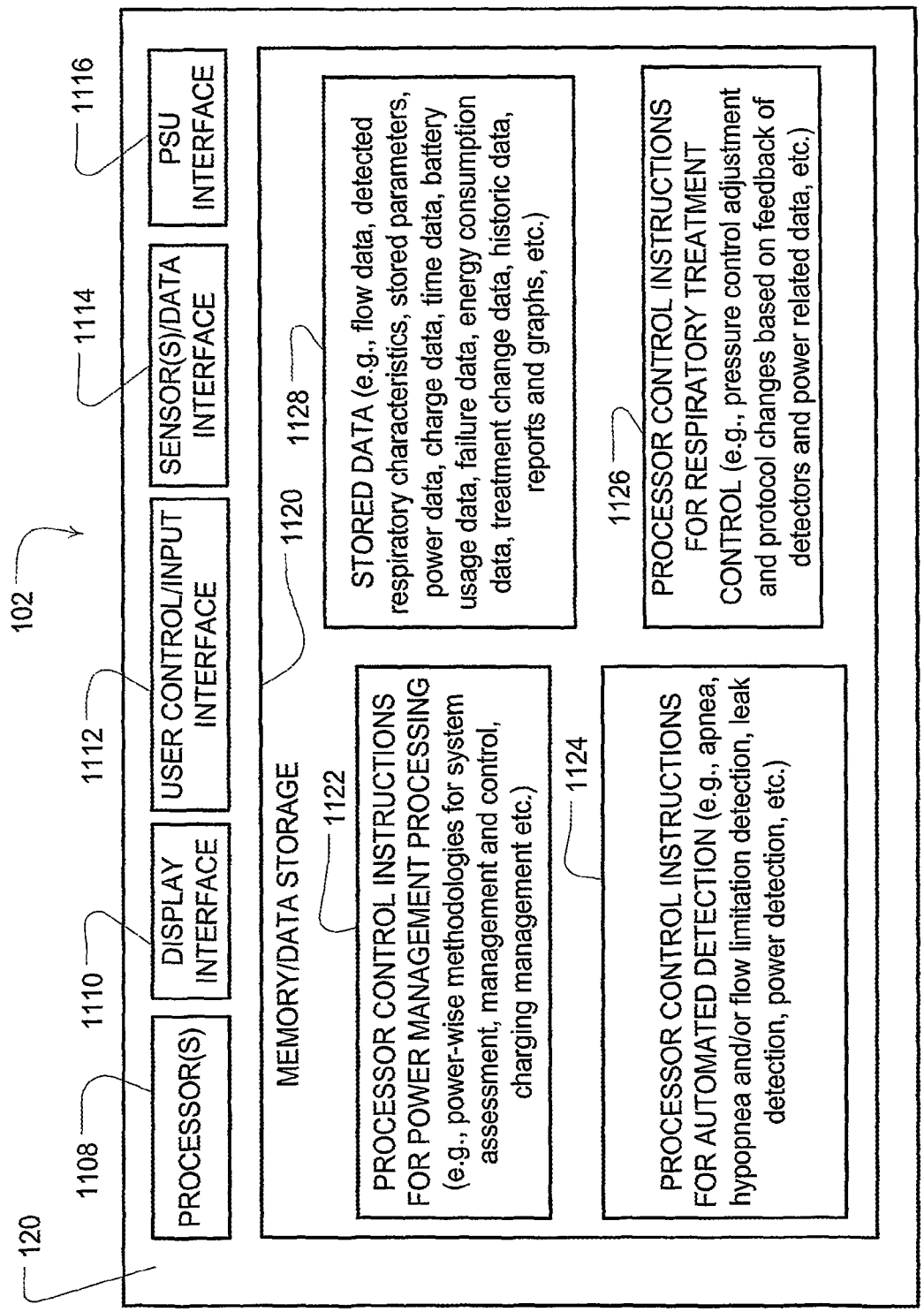
FIG. 11 is a block diagram of a power-wise controller in an example embodiment of the present technology.

An example architecture of a controller 120 is illustrated in the block diagram of FIG. 11. In the illustration, the controller may be implemented by one or more programmable processors 1108. The device may also include a display interface 1110 to output data for the user as previously discussed (e.g., power data, stored parameters, charge data, treatment data etc.) to a display such as on a monitor, LCD panel, touch screen, etc. A user control/input interface 1112, for example, for a keyboard, touch panel, control buttons, mouse etc. may also be included as for inputting data, or otherwise activating, adjusting or operating the methodologies described herein. The device may also include a component, sensor or data interface 1114, such as a bus, for receiving/transmitting data between components or the device and other devices such as for programming instructions, settings data and other output or input data as previously described. The device may also include a power supply unit 1116 or an interface for same.

The device also includes memory/data storage components 1120 containing control instructions and data of the aforementioned methodologies. For example, at 1122, they may include stored processor control instructions for the power management processing such as the power-wise methodologies of the system for assessment, management and control of the power components, charging management, etc. At 1124, these may also include stored processor control instructions for automated detection methodologies such as apnea, hypopnea and/or flow limitation detection, leak detection, power detection, etc. At 1126, these may also include stored processor control instructions for automated methodologies for respiratory treatment control such as feedback processing and pressure or flow control adjustment according to the power related conditions and power-wise methodologies, etc. Finally, they may also include stored data at 1128 for the methodologies such as flow data, detected respiratory characteristics, stored parameters, power data, charge data, time data, battery usage and maintenance data, power failure data, energy consumption data, treatment change data, historic data, reports, graphs, etc.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

For example, although embodiments of a bus system have been described in terms of a master-slave configuration, other communications schemes may also be implemented. For example, communications of the system may be implemented as dispersed logic system or chaotic system. Such systems may permit multiple negotiations in a manner unavailable with a master-slave configuration. Similarly, although a three-wire system is discussed, other bussing configurations may be utilized. Communications between components of the apparatus may even optionally be implemented by wireless schemes such by implementing a system with infrared or Bluetooth communications between components.

The invention claimed is:

1. In a respiratory treatment apparatus, a method comprising:
    storing data included in one or more energy profiles in a memory, each energy profile representing energy information for operation of one or more components of the respiratory treatment apparatus at particular settings with respect to time, and each energy profile including prioritization indicia to prioritize certain components of the respiratory treatment apparatus over other components of the respiratory treatment apparatus based on patient needs;
    controlling a flow generator of the respiratory treatment apparatus to provide a flow of breathable gas to a patient;
    detecting available energy of a power supply unit powering the respiratory treatment apparatus; and
    changing a treatment regime provided by the respiratory treatment apparatus based on the detection of available energy and the one or more energy profiles.

2. The method of claim 1 wherein the detecting comprises determining information representative of a discharge rate of a battery of the power supply unit.

3. The method of claim 1 wherein the changing of a treatment regime comprises controlling a pressure treatment regime that is different from a pressure treatment regime previously provided by the apparatus.

4. The method of claim 1 wherein the changing of a treatment regime comprises controlling a temperature of a pressure treatment regime that is different from a temperature of a pressure treatment regime previously provided by the apparatus.

5. The method of claim 1 wherein the changing of a treatment regime comprises selecting a mode of operation associated with an energy profile of the one or more energy profiles, the associated energy profile representing a quantification of energy consumption of an operation of at least one component of the respiratory treatment apparatus so that the detected available power is sufficient to satisfy the quantification of energy of the energy profile.

6. A respiratory treatment apparatus comprising:
a flow generator to provide a flow of breathable gas to a patient;
a memory to store data included in one or more energy profiles, each energy profile representing energy information for operation of one or more components of the respiratory treatment apparatus at particular settings with respect to time, and each energy profile including prioritization indicia to prioritize certain components of the respiratory treatment apparatus over other components of the respiratory treatment apparatus based on needs of the patient;
a power supply unit; and
a controller coupled with the flow generator, the memory and the power supply unit, the controller being configured to detect an available power of the power supply unit and to control a change to a treatment regime provided by the respiratory treatment apparatus as a function of the detection of available power and based on the one or more energy profiles.

7. The apparatus of claim 6 further comprising a current sensor and wherein the controller determines a discharge rate of a battery of the power supply unit in conjunction with a signal from the current sensor.

8. The apparatus of claim 6 wherein the change to the treatment regime comprises controlling a pressure treatment regime that is different from a pressure treatment regime previously provided by the apparatus.

9. The apparatus of claim 6 further comprising a heating element controlled by the controller wherein the change to the treatment regime comprises controlling a temperature of a pressure treatment regime that is different from a temperature of a pressure treatment regime previously provided by the apparatus.

10. The apparatus of claim 6 wherein the controller is configured to change the treatment regime by selecting a mode of operation associated with an energy profile of the one or more energy profiles, the associated energy profile representing a quantification of energy consumption of an operation of at least one component of the respiratory treatment apparatus so that the detected available power is sufficient to meet the quantification of energy of the energy profile.

11. The apparatus of claim 6 wherein the controller is configured to store data representing the change to the treatment regime and the detection of power and to generate output of the change to the treatment regime and the detection of power represented by the stored data to a user of the apparatus.

12. A respiratory treatment apparatus comprising:
a flow generator to provide a flow of breathable gas to a patient;
a memory to store data included in one or more energy profiles, each energy profile representing energy information for operation of one or more components of the respiratory treatment apparatus at particular settings with respect to time, and each energy profile including prioritization indicia to prioritize certain components of the respiratory treatment apparatus over other components of the respiratory treatment apparatus based on needs of the patient;
a power supply unit including at least one battery; and
at least one processor coupled with the flow generator, the memory and the power supply unit, the processor including control instructions to control a detection of an available power of the power supply unit and to control a change to a treatment regime provided by the respiratory treatment apparatus as a function of the detection of available power and based on the one or more energy profiles.

13. The apparatus of claim 12 further comprising a current sensor and wherein the instructions of the processor control a calculation of a discharge rate of the at least one battery in conjunction with a signal from the power sensor.

14. The apparatus of claim 12 wherein the change to the treatment regime comprises a pressure treatment regime that is different from a pressure treatment regime previously provided by the apparatus.

15. The apparatus of claim 12 further comprising a heating element controlled by the processor and wherein the change to the treatment regime comprises a temperature of a pressure treatment regime that is different from a temperature of a pressure treatment regime previously provided by the apparatus.

16. The apparatus of claim 12 wherein the instructions of the processor are configured to change the treatment regime by selecting a mode of operation associated with an energy profile of the one or more energy profiles, the associated energy profile further comprising a quantification of energy consumption of an operation of at least one component of the respiratory treatment apparatus so that the detected available power is sufficient to meet the quantification of energy of the energy profile.

17. The apparatus of claim 12 wherein the control instructions further comprise storing data representing the change to the treatment regime and the detection of power and generating output of the change to the treatment regime and the detection of power represented by the stored data to a user of the apparatus.

* * * * *